(12) United States Patent
Simon et al.

(10) Patent No.: US 8,263,112 B2
(45) Date of Patent: *Sep. 11, 2012

(54) IN VIVO USE OF WATER ABSORBENT POLYMERS

(75) Inventors: Jaime Simon, Angleton, TX (US); Alan D. Strickland, Lake Jackson, TX (US)

(73) Assignee: Sorbent Therapeutics, Inc., Sunnyvale, CA (US)

( * ) Notice: Subject to any disclaimer, the term of this patent is extended or adjusted under 35 U.S.C. 154(b) by 267 days.

This patent is subject to a terminal disclaimer.

(21) Appl. No.: 10/840,112

(22) Filed: May 6, 2004

(65) Prior Publication Data

US 2005/0031680 A1 Feb. 10, 2005

Related U.S. Application Data

(63) Continuation-in-part of application No. 10/036,989, filed on Nov. 6, 2001, now Pat. No. 6,908,609.

(60) Provisional application No. 60/249,955, filed on Nov. 20, 2000.

(51) Int. Cl.
*A61K 9/16* (2006.01)

(52) U.S. Cl. ......... 424/439; 424/451; 424/464; 424/489

(58) Field of Classification Search .............. 424/79, 424/81, 106, 112, 438, 180, 463, 439, 451, 424/464, 489; 536/56, 106, 112; 514/892, 514/867

See application file for complete search history.

(56) References Cited

U.S. PATENT DOCUMENTS

| | | | | |
|---|---|---|---|---|
| 4,143,130 A | * | 3/1979 | Imondi et al. | 424/78.33 |
| 4,470,975 A | * | 9/1984 | Berger et al. | 514/54 |
| 4,605,701 A | | 8/1986 | Harada et al. | 525/107 |
| 4,670,287 A | * | 6/1987 | Tsuji | 424/463 |
| 5,004,603 A | * | 4/1991 | Thompson | 424/78.35 |
| 5,051,253 A | | 9/1991 | Lloyd-Jones et al. | 424/81 |
| 5,215,754 A | * | 6/1993 | Valorose et al. | 424/474 |
| 5,487,888 A | | 1/1996 | Mandeville, III et al. | 424/78.1 |
| 5,516,524 A | * | 5/1996 | Kais et al. | 424/439 |
| 5,607,669 A | | 3/1997 | Mandeville, III et al. | 424/78.12 |
| 5,618,530 A | | 4/1997 | Mandeville, III et al. | 424/78.12 |
| 5,679,717 A | | 10/1997 | Mandeville, III et al. | 514/742 |
| 5,693,675 A | | 12/1997 | Mandeville, III et al. | 514/742 |
| 5,702,696 A | | 12/1997 | Mandeville, III et al. | 424/78.12 |

FOREIGN PATENT DOCUMENTS

| | | | |
|---|---|---|---|
| EP | 077 956 | * | 8/1982 |
| EP | 0077956 | * | 10/1982 |
| JP | 10130154 | | 5/1988 |
| JP | 10059851 A | | 6/1996 |
| JP | 1059851 | | 3/1998 |
| WO | WO 98/17707 | | 4/1998 |

* cited by examiner

*Primary Examiner* — Michael G Hartley
*Assistant Examiner* — Jagadishwar Samala
(74) *Attorney, Agent, or Firm* — K&L Gates LLP

(57) ABSTRACT

The subject invention is a method and material for removing fluid from the intestinal tract of a host and may be useful in treating animals or human patients suffering from fluid overload states. In one embodiment, the subject method involves ingesting an enterically coated non-systemic, non-toxic, non-digestible, water absorbing polymer which absorbs fluid while passing through the intestinal tract. The polymer is excreted in the feces wherein the polymer and absorbed fluid is removed from the body. Preferred polymers include super absorbent acrylic acid polymers, preferably provided in bead form. The polymers may include functional groups for selectively removing blood borne waste products, e.g. urea, from the G.I. tract.

13 Claims, No Drawings

IN VIVO USE OF WATER ABSORBENT POLYMERS

CROSS-REFERENCE TO A RELATED APPLICATION

This Application is a continuation-in-part of U.S. application Ser. No. 10/036,989 filed Nov. 6, 2001 now U.S. Pat. No. 6,908,609 and claims the benefit under 35 USC 119(e) of U.S. provisional application No. 60/249,955 filed Nov. 20, 2000 incorporated herein by reference.

BACKGROUND OF THE INVENTION

Fluid overload states are associated with a number of serious medical conditions. Many cardiac diseases can lead to compromise in the heart's ability to pump blood. Myocardial infarction frequently causes the replacement of heart muscle by fibrotic tissue. This fibrotic tissue is not capable of pumping blood and results in a decrease in the cardiac output. Cardiomyopathy causes the heart muscle to have less strength resulting in reduced cardiac output. These and other cardiac diseases result in blood pooling in the pulmonary vasculature and even in peripheral tissues such as the feet and legs. This congestive heart failure can cause fluid to leak from the vascular space into the extravascular space to cause edema of the tissue involved, e.g. pulmonary edema, edema of the legs, etc. The reduced cardiac output causes lowered blood flow to the kidneys which decreases the urinary output. Diseases of the kidney can also lead to fluid overload states. For example, nephrosis and nephritis cause decreases in the ability of the kidney to excrete urine with resultant fluid retention in the body and formation of edema. Acute and chronic renal failure compromise or eliminate the production of urine, resulting in fluid overload of the body. Intestinal or nutritional disorders can result in decreased serum protein levels. Particularly when the serum albumin levels are decreased, the colloidal pressure in the vascular space is inadequate to retain fluid in the blood vessels and tissue edema forms. These fluid overload states can result from, among other diseases, kwashiorkor, gluten-sensitive enteropathy, and deficiencies of such digestive enzymes as chymotrysin or carboxypeptidase. Hepatic disease can also lead to fluid overload states. Cirrhosis of the liver can result from many liver diseases including any of the hepatitis viruses, alcoholic liver disease, biliary obstructions, hemochromatosis, Wilson's disease, mucopolysaccharidoses, and many other genetic diseases. Cirrhosis of the liver results in decreased synthesis of serum proteins such as albumin. It also causes obstruction to blood flow from the body below the diaphragm to the heart. This obstruction causes increased pressure the vasculature with resultant edema formation below the diaphragm, ascites formation, and decreased blood flow to the kidneys. Disorders of other systems, such as the endocrine (e.g. preeclampsia, eclampsia, etc.), neurological (e.g. angioneurotic edema, etc.), or immune systems can also cause fluid overload states. Hormonal alterations, such as the syndrome of inappropriate antidiuretic syndrome and states with high progesterone levels, can result in fluid retention and overload. Pulmonary diseases, such as pulmonary fibrosis and chronic obstructive pulmonary diseases, also result in fluid overload states. This listing of diseases and syndromes is merely illustrative of some of the conditions which can cause fluid overload states and is not intended to be exhaustive.

In addition to the fluid overload, many of these conditions cause buildup of other substances. Any condition that compromises urinary output can result in increases in urea, creatinine, other nitrogenous waste products, and electrolytes or minerals such as sodium, phosphate, and potassium. Hepatic diseases can result in retention of water along with substances normally processed by the hepatocytes such as ammonia and various organic acids. Cardiac disorders can result in build up of lactic acid or lactates due to ischemia of various tissues.

In addition to conditions that cause fluid overload, there are many medical conditions where fluid is not being appropriately distributed throughout the body, whether or not there is actual excess of total body fluid, referred to herein as "fluid mal-distribution states". These conditions include such conditions as altitude sickness, diabetes, physiological changes of aging, some types of nocturia, some types of pre-menstrual syndrome, capillary protein leak syndrome, pregnancy, some forms of hypertension, post operative fluid retention, obesity, chronic renal insufficiency, side effects from chemotherapy, and others. Nocturia, the need for passage of urine more than twice during the night, has many causes. Some patients have an overactive bladder which awakens them several times per night. Other patients have an osmotic diuresis during the night, such as glucosuria in diabetic patients. Many patients have a fluid diuresis during the night secondary to saline retention during the day. Such saline retention typically occurs with fluid accumulation in the dependent extremities. During the night, the extremities are repositioned to be at the same level as the heart, and the saline diuresis begins. These patients frequently pass 500 to 1500 mL of urine per night. Since the normal bladder capacity is about 250 mL, these patients may have nocturnal micturition as many as five times per night. Hypertension is another symptom which may result from fluid overload or fluid mal-distribution. Such patients can frequently be identified by their response to a diuretic. A patient with fluid-responsive hypertension will usually show a decrease in systolic and/or diastolic blood pressure after a dose of rapid acting diuretic or a dialysis procedure. However, such patients resist chronic administration of diuretics since these medications interfere severely with quality of life and sleep. Even hypertension that is not responsive to acute fluid removal, such as vaso-constrictive hypertension, may respond to chronic administration of diuretics.

If untreated, the build up of water (i.e. fluid overload) and other blood borne waste products can lead to unpleasant symptoms and serious medical complications. Peripheral edema can be painful and cause clothing to be too tight. The swelling from the edema can compromise the blood flow to or from the tissues resulting in infections or ulcers. Pulmonary edema causes difficulty in absorbing enough oxygen to properly oxygenate tissues. Ascites can be quite painful. Edema of the intestine secondary to liver disease causes malabsorption of nutrients leading to malnutrition. Disease of the kidney can cause build up of uremic toxins such as putrescine, xanthine, and creatinine. Ammonia retention can result in neurological damage. Any organic acid in excess can cause metabolic acidosis with resultant dysfunction of pH dependent processes such as enzymatic metabolic reactions. Ischemic tissues with increased lactic acid can be compromised in function or even necrose.

Treatment for fluid overload states involves both removal of the excess fluid and remediation of the other waste products that are accumulating in the body. Removal of the waste products may be quite different from the treatment for removal of water and may have a different degree of success. A common method of treatment for removal of excess water is fluid restriction. When fluid intake is less than the fluid output through urinary losses, fecal losses, and insensible losses (e.g. sweat, moisture in the breath, etc.), fluid is removed from the body and the fluid overload state can be treated. This method of treatment is not usually adequate for fluid removal and is not designed to remove other metabolic wastes. As such, it is not usually the sole treatment of a fluid overload state.

Another common treatment for fluid overload states is administration of diuretic agents. Diuretic agents alter the normal kidney function to either increase the amount of plasma filtrate produced or decrease the reabsorption of tubular fluid. These agents usually interfere with the normal renal handling of electrolytes. For instance, furosemide interferes with normal sodium reabsorption from the tubules and results in excessive wasting of sodium and potassium. Increasing the dietary sodium usually worsens the fluid overload state, but not increasing the dietary sodium frequently results in decreased total body sodium and decreased serum sodium concentrations. This eventually makes the patient resistant to the diuretic. Diuretic resistance may also result from the fluid overload being confined to the extravascular space while the diuretic can only alter the retention of fluid in the intravascular space.

Dialysis is a common treatment for those suffering from fluid overload states and toxic accumulations of metabolic wastes. Both compromised renal function and compromised hepatic function have been treated with dialysis. Dialysis most commonly takes one of two forms, hemodialysis or peritoneal dialysis. Both forms of dialysis remove excess water and waste products (e.g. urea, salts, etc.) from the body. However, hemodialysis and peritoneal dialysis involve significant patient discomfort and/or inconvenience. In addition, removal of water and wastes through dialysis is not uniform for all substances. Sodium and potassium are easily removed during either peritoneal dialysis or hemodialysis. Urea is relatively easily removed. Creatinine and phosphate have lower removal rates, and proteins such as beta-2-microglobulin have markedly lower clearances. Removal rates for hepatic toxins are quite low unless modifications are made to the typical hemodialysis equipment and solutions. One method being used is to add albumin to the dialysate to facilitate removal of toxins which are carried on albumin in the bloodstream.

WO 98/17707 to Simon et. al. published Apr. 30, 1998 describes the therapeutic ingestion of functionalized, water soluble, polyether glycol polymers for the selective absorption of certain blood borne waste (i.e. phosphate and/or oxalate) from in the gastrointestinal (GI) tract. However, the object of this invention is to prevent the absorption of dietary phosphate and oxalate and does not address fluid overload. This reference is incorporated herein by reference.

Ingestion of oxystarch and coal for treatment of end stage renal dialysis patients has been investigated by Friedman et. al., see Clinical Aspects of Uremia and Dialysis, pg. 671-687 (1977) and see Friedman, et. al., "Combined oyxstarch-charcoal trial in uremia: sorbent-induced reduction in serum cholesterol" Kidney International 1976; 7: S273-6. The aldehydes on the oxystarch are intended to remove urea and the charcoal is intended to remove other organic substrates. However, the fluid capacity of these polymers is limited and not clinically practical as a fluid overload agent.

U.S. Pat. Nos. 5,679,717; 5,693,675; 5,618,530; 5,702,696; 5,607,669; 5,487,888 and 4,605,701 describe the ingestion of a crosslinked alkylated amine polymers to remove bile salts and/or iron from a patient. Again these polymers are limited in their ability to absorb fluids and are not practical for treatment of fluid overload.

U.S. Pat. No. 4,470,975 describes the elimination of water from the gastrointestinal (GI) tract by ingesting an insoluble, hydrophilic crosslinked polysaccharide which absorbs water from the gastrointestinal (GI) tract and is subsequently excreted. This patent is incorporated herein by reference. Unfortunately, the described polysaccharides can be difficult to synthesize and relatively expensive. Moreover, their ability to absorb water or saline on a per-weight basis is limited; thus leading to very high doses to the patient in order to obtain an effective treatment.

Imondi, A. R. and Wolgemuth, R. L reported in "Gastrointestinal sorbents for the treatment of uremia. I. Lightly cross-linked carboxyvinyl polymer" in Ann. Nutr. Metab. 1981; 25: 311-319 on studies of several insoluble resins, two polysaccharide preparations, various oxystarch preparations, and a highly swellable polyacrylic acid for oral use in treating uremia. They note that the polyacrylic acid increased the fecal excretion of urea and total nitrogen to the same extent as oxystarch. Ammonia, sodium, potassium, calcium, and magnesium were removed by the polyacrylic acid while phosphate, the only anionic species investigated, was not removed by the polyacrylic acid. Oxystarch and the polyacrylic acid increased fecal fluid excretion to the same degree—which is inadequate for clinical utility, as revealed above in the discussion of Friedman's articles on oxystarch.

Japanese Patent Application Kokai No. H10-59851 (Application No. H8-256387) and Japanese Patent Application Kokai No. H10-130154 (Application No. H8-286446) disclose the oral administration of alkali metal and alkaline earth salts of crosslinked polyacrylates to treat kidney disease. These polymers are administered orally from an oil emulsion. Thus, the water absorption effect of the polymer begins within the stomach, just as is the case in the experiments reported by Imondi and Wolgemuth. Such direct exposure to stomach acid can lead to significant polymer degradation due to the low pH environment. Moreover, the polymer tends to absorb nutrients from the body via the stomach along with becoming saturated with fluid just ingested rather than fluid containing uremic wastes such as urea and creatinine. Thus, although the disclosed polymers absorb significantly more water or saline than polysaccharides on a per weight basis, direct exposure to stomach acid can result in undesired polymer degradation, absorption of nutrients, and polymer saturation with ingested fluid rather than the absorption of excess fluid and waste from the intestinal tract.

U.S. Pat. No. 4,143,130 discloses the oral administration of lightly crosslinked polyacrylic acid for removing calcium from the intestinal tract in order to treat kidney stones. The polymer may be provided as a gel with hydroxyethylcellulose in a tablet, capsule or pill form which may be enterically coated, although no examples are provided. The aim of this invention was to remove calcium from the body—not fluids. In fact the preferred method of administration included adding water to the formulation prior to administering to the patient. Thus, there was no suggestion that this polymer could be used to treat fluid overload states or remove metabolic waste products or fluid from the intestinal tract.

U.S. Pat. No. 5,051,253 discloses the oral administration of polyacrylic acid for treating mucolytic protease activity in patients with inflammatory bowel disease. The polymer may be provided with a EUDRAGIT coating. The aim of this invention was to administer small amounts of a gel to the colon to coat the mucosa and protect it from degradation by protease. Treatment of fluid overload was not suggested. Removal of metabolic wastes was not anticipated or desired.

Polycarbophil is a synthetic oral bulk-producing laxative based upon the calcium salt of polyacrylic acid. Calcium polycarbophil can absorb up to 60 times its weight in water or 6 times its weight in 0.9% saline. Polycarbophil is known for use in the treatment of constipation and diarrhea and is commonly orally administered with 250 milliliters of water per 500 mg dose.

Although these literature references evidence attempts to provide orally administered substances, such as polysaccharides, polystarches, polyaldehydes, activated charcoal, and polyacrylic acid compounds, none evidence a successful approach to removing fluid from the GI tract. Most of the agents have had inadequate fluid absorbing capacity. Agents with larger capacities for fluid absorption, i.e. sodium polyacrylate or potassium polyacrylate, were not disclosed as agents for treatment of fluid overload states or for absorption of fluid from the GI tract. Calcium polyacrylate, which does not absorb as much fluid (see Japanese Patent Application Kokai No. H10-130154, Application No. H8-286446, see Claim 5 and Table 1) was chosen by one group. Polyacrylic acid, which also does not absorb a large amount of fluid, was chosen by the other group and was directed at prevention of renal stones rather than treatment of fluid overload or removal of fluid from the GI tract (see U.S. Pat. No. 4,143,130). No explanations of these choices are given. The current investigators have found that orally administered polyacrylates exposed to acidic conditions common in the stomach do not absorb fluid as well after exposure to acid, begin their absorption of fluid in the stomach where most fluid is recently ingested fluid, and interfere with normal absorption of nutrients and medications.

Therefore, there continues to be a need for an effective means for removing fluid from the GI tract of a host, removing fluid that is poorly distributed in a host, and for treatments for fluid overload states. Such a treatment should ensure fluid removal occurs substantially in the intestinal tract rather than the stomach, thus avoiding polymer degradation, absorption of nutrients and saturation with ingested fluid. Furthermore, treatments are sought which can selectively remove blood borne waste products, e.g. urea, phosphate, salts, etc.

SUMMARY OF THE INVENTION

The subject invention is a method and material for removing fluid (e.g. water) from the intestinal tract of a host. The subject method may be useful in the treatment of patients suffering from fluid overload states or patients suffering from mal-distribution of fluid. Fluid overload states can result from a variety of conditions including, but not limited to, congestive heart failure, cirrhosis of the liver, nephrosis, ascites, renal disease, edema such as that associated with chemotherapy, pre-menstrual fluid overload, and preeclampsia. Fluid mal-distribution states include, but are not limited to altitude sickness, diabetes, physiological changes of aging, nocturia, pre-menstrual syndrome, capillary protein leak syndrome, pregnancy, some forms of hypertension, post operative fluid retention, obesity, chronic renal insufficiency, and side effects from chemotherapy. The subject method involves directly delivering a non-systemic, non-toxic, non-digestible, fluid absorbing polymer to the intestinal tract where it absorbs fluid as it passes therethrough and is subsequently excreted. In one embodiment, the means for directly delivering the polymer comprising enterically coating the polymer and ingesting (orally administering) the polymer to the patient. The enteric coating protects the polymer from exposure to the stomach. After passing through the stomach of the host, the coating breaks down wherein the polymer is exposed to the intestinal tract, i.e. "directly delivered."

Applicable polymers include polyelectrolyte and non-polyelectrolyte compounds. Polyelectrolyte polymers include, but are not limited to, carboxylate containing polymers such as polyacrylates, polyaspartates, polylactates, and the like, sulfonate containing polymers, and physiologically quaternary or cationic amine containing polymers such as polyallylamine or polyethyleneimine. Non-polyelectrolyte polymers, or non-ionic polymers, include such polymers as polyacrylamide gels, polyvinyl alcohol gels, and polyurethane gels. Preferred polymers include "super absorbent" acrylic polymers. The invention may include mixtures of other polymers in addition to the water absorbing polymers. Some polymers in this mixture may include functional groups for selectively removing blood borne waste products e.g. urea, from the G.I. tract. One modality of this invention involves the use of multiple polymer components to remove water and a series of waste products. The subject polymers may be enterically coated such that they are protected from stomach acid but are exposed or "released" in the intestinal tract. Alternatively, the subject polymers may be administered through means, such as intestinal tubes, which allow placement directly into the intestine.

The present invention can reduce the number of dialysis treatments, amount of dialysis treatment time required and/or completely alleviate the need for conventional dialysis. The present invention can remove fluid from animals or patients with congestive heart failure, ascites, and other fluid overload conditions. The present invention can also remove fluid from animals or patients with fluid mal-distribution states such as nocturia, fluid-responsive hypertension, and others. The present invention can also remove waste products from animals or patients.

The polymers of the subject invention are generally easy to produce and many are commercially available.

The enteric coatings used to encapsulate or coat the subject polymers ensure that fluid removal occurs substantially in the intestine rather than the stomach. By preventing the polymers from becoming active in the stomach, the present invention also allows the polymers to absorb more fluid secreted into the intestinal tract which contains metabolic waste products rather than recently ingested dietary fluids. In contrast to previous art cited above, the present invention protects the polymers from exposure to gastric acid, thereby improving the fluid absorbing performance. By preventing the polymers from absorbing fluid in the proximal small intestine, the present invention has less interference with normal absorption of nutrients and medications than the absorbents mentioned in prior art.

DETAILED DESCRIPTION OF THE INVENTION

The subject invention involves directly delivering a non-systemic, non-toxic, non-digestible, water-absorbing polymer to the intestinal tract of a host to remove fluid therefrom. The term "directly delivered" is intended to mean that the polymer is not directly exposed to the stomach prior to deliver to the GI tract. One preferred means of directly delivering the polymer to the GI tract is via oral administration of an enterically coated polymer. The enteric coating protects the polymer as it passes through the stomach such that the polymer does not significantly degrade as a result of exposure to stomach acid. Moreover, the enteric coating prevents significant absorption or adsorption of nutrients or water from the stomach. Upon reaching the intestinal tract, the enteric coating exposes or "releases" the polymer where water and toxins are then absorbed. The polymer is subsequently excreted in the feces wherein the polymer, absorbed water and toxins are removed from the body. Other non-limiting examples of direct delivery include: introduction using an enema, a tube that is placed through the nose or mouth and empties directly into the desired portion of the intestine, a tube surgically implanted through the abdomen that empties into the intestine, and via colonic lauage administration.

The subject polymers include crosslinked polyacrylates which are water absorbent such as those prepared from α,β-ethylenically unsaturated monomers such as monocarboxylic acids, polycarboxylic acids, acrylamide and their derivatives, e.g. polymers having repeating units of acrylic acid, methacrylic acid, metal salts of acrylic acid, acrylamide, and acrylamide derivatives (such as 2-acrylamido-2-methylpropanesulfonic acid) along with various combinations of such repeating units as copolymers. Such derivatives include acrylic polymers which include hydrophilic grafts of polymers such as polyvinyl alcohol. Examples of suitable polymers and processes, including gel polymerization processes, for preparing such polymers are disclosed in U.S. Pat. Nos. 3,997,484; 3,926,891; 3,935,099; 4,090,013; 4,093,776; 4,340,706; 4,446,261; 4,683,274; 4,459,396; 4,708,997; 4,076,663; 4,190,562; 4,286,082; 4,857,610; 4,985,518; 5,145,906; and 5,629,377, which are incorporated herein by reference. In addition, see Buchholz, F. L. and Graham, A. T., "Modern Superabsorbent Polymer Technology," John Wiley & Sons (1998). Preferred polymers of the subject invention are polyelectrolytes. The degree of crosslinking can vary greatly depending upon the specific polymer material; however, in most applications the subject superabsorbent polymers are only lightly crosslinked, that is, the degree of crosslinked is such that the polymer can still absorb over 10 times its weight in physiological saline (i.e. 0.9% saline). For example, such polymers typically include less than about 0.2 mole percent crosslinking agent.

Different morphological forms of the polymers are possible. Polymers discussed in Buchholz, F. L. and Graham, A. T. "Modern Superabsorbent Polymer Technology," John Wiley & Sons (1998) are generally irregularly shaped with sharp corners. Other morphological forms of crosslinked polyacrylates can be prepared by techniques discussed in EP 314825, U.S. Pat. No. 4,833,198, U.S. Pat. No. 4,708,997, WO 00/50096 and U.S. No. 1999-121329 incorporated herein by reference. These include several methods for preparing spherical bead forms and films. The bead forms, as prepared by methods similar to Example 1 of EP 314825 or Example 1 or Example 2 in WO 00/50096, are particularly advantageous for the present invention because the uptake of fluid and the swelling are more gradual (See Example 6 below). The irregularly shaped polymer reaches its maximum fluid absorption within 2 hours of placement into saline. Since the normal transit time through the stomach is 1.5 hours and the normal transit time through the small intestine is 1.5 hours, most of the fluid absorption of this polymer would occur in the small intestine. The bead form of the polymer swells to its maximum extent 10 hours after being exposed to saline. This allows the bead form of polymer to absorb more fluid in the distal small intestine and colon than occurs with the irregularly shaped polymer form. Absorbing more fluid in the distal portion of the intestine prevents interference with the normal intestinal absorption of nutrients and drugs while absorbing fluid that has a higher concentration of waste products. Swelling of the polymer in the colon also prevents feelings of fullness or bloating that may occur when the swelling occurs in the stomach.

Many of these polymers, regardless of the morphological form, are known for use as "super absorbents" and are commonly used in controlled release applications and personal hygiene products. For the subject invention, food and/or pharmaceutical grades of materials are preferred. Although the alkali metal and alkaline metal salts of these polymers can be used (e.g. calcium, potassium, etc.); the sodium salt is particularly preferred.

Preferably the subject polymers are capable of absorbing at least about 10 times their weight in physiological saline. In several embodiments the subject polymers are capable of absorbing more than 20 times, 30 times, and even above 40 times their weight in physiological saline. For purposes of this document, the term saline shall refer to physiological saline which comprises a 0.9% saline solution, consistent with that found in the body.

Although less preferred due to their inability to absorb as much fluid as the polymers described above, polysaccharides may be used in the subject invention, so long as such polysaccharides are directly administered to the intestinal tract and are not exposed to the stomach. For example, the polysaccharides described in U.S. Pat. No. 4,470,975 may be formulated as a tablet or provided within a capsule which is enterically coated and orally administered. In several embodiments of this invention, polysaccharide polymers are specifically avoided.

In several embodiments, the subject polymer includes functional groups which selectively bind with blood borne waste products, e.g. urea, while passing through the gastrointestinal tract. Such functional groups include, but are not limited to aldehyde groups for binding urea, six to twelve carbon atom hydrocarbon substituents for binding urea, polyaminoalkylene substituents such as triethylenetetramine or tetraethylenepentamine for binding oxalate. Additionally, amine functional groups, e.g. ammonia, ethyleneamines, alkanol amines, $C_1$-$C_{10}$ alkyl amines may be used for binding phosphate or oxalates. Thus, such "functionalized" polymers can be designed to simultaneously absorb water along with selectively binding with one or more blood borne waste products. As part of a treatment regime, it may be desirable to alternate or otherwise vary the use of some functionalized polymers depending upon the need for removal of the target waste product. Moreover, multiple polymers including different functional groups may be used in combination, alternated or otherwise combined for specialized treatment regimes.

In one embodiment of invention, the subject polymers are coated or encapsulated with an enteric material which prevents the release of polymer in the stomach and delivers the polymer to the intestine. The preferred delivery site is the distal ileum or colon. Examples of such suitable coatings include hydroxypropylmethyl cellulose, hydroxypropylmethyl cellulose phthalate, cellulose acetate phthalate, and sodium carboxyl methyl cellulose. Other suitable coatings are known in the art, e.g. polymers based on methacrylic acid and its derivatives, such as the EUDRAGIT pH dependent copolymers, and are included within the scope of the present invention. The polymer may be provided within a capsule that is subsequently enterically coated. Multiple coatings may be utilized. When provided in bead or tablet form, the polymer may be directly coated. As previously mentioned, this invention includes other methods of delivering the subject polymers to the intestinal tract.

The quantity of water absorbent polymer utilized in a given treatment varies depending upon the total amount of water the patient normally excretes through the renal route or through dialysis, along with the particular type of polymer utilized. Since the water intake of patients varies greatly, the amount of water that must be removed also varies. Thus, an effective amount of water absorbent polymer will generally have a wide range, e.g. from about 0.5 grams to about 40 grams per treatment but in some instances can be as high as about 100 grams per treatment.

The present invention has particular applicability for fluid mal-distribution states such as, for example, altitude sickness, diabetes, physiological changes of aging, nocturia, pre-menstrual syndrome, capillary protein leak syndrome, pregnancy, some forms of hypertension, post operative fluid retention, obesity, chronic renal insufficiency, side effects of chemotherapy. The present invention is particularly preferred for the treatment of nocturia or fluid-responsive hypertension.

EXAMPLES

Example 1

A bead form of absorbent polymer based on a partial sodium salt of lightly crosslinked polyacrylic acid was prepared in a fashion similar to that given in Example 1 of EP 314825. Acrylic acid, neutralized with sodium hydroxide and dissolved in water, was mixed with the pentasodium salt of diethylenetriaminepentaacetic acid and added to a reactor charged with Isopar L and Aerosil R972 held at 65° C. Trimethylolpropane triacrylate and a solution of sodium persulfate were added with vigorous stirring. The product of the reaction was removed from the reactor, filtered, washed with ethanol, and dried under vacuum. The resultant polymer had an absorbance capacity of 45 gram 0.9% saline solution per gram of polymer.

Example 2

The bead form of polymer from Example 1 was coated with a 5% coating of hydroxypropylmethylcellulose followed by a subsequent enteric coating of a 17.5% coating of Sureteric (polyvinyl acetate phthalate).

Example 3

Six male beagle dogs underwent removal of the right kidney and ligation of seven of the eight branches of the left renal artery. Following one week of recovery time, the blood chemistries revealed that all of the dogs were in renal failure. Two dogs were then started on 1 gram of polymer from Example 1 per kg body weight per day in two divided doses given with food. Two more dogs were started on 1 gram of polymer as the enteric coated beads from Example 2 in two divided doses given with food. Two dogs were followed as controls. On the seventh and fourteenth day of receiving the polymer, each dog was given capsules containing a total of 73 mg ampicillin, 38 mg phenobarbital, and 8.8 mg zinc simultaneously with the dose of polymer. Blood was drawn just before and again two hours after the capsules were given. Serum ampicillin rose to an average of 2.3 mg/L in the control dogs, 1.4 mg/L in the dogs given uncoated polymer, and 2.6 mg/L in the dogs given the enteric coated polymer. Serum phenobarbital levels rose to an average of 5.1 mg/L in the control dogs, 2.7 mg/L in the dogs receiving uncoated polymer, and 5.0 mg/L in the dogs receiving the enteric coated polymer. Serum zinc levels rose by 0.4 ppm in the control dogs, fell by 0.8 ppm in the dogs receiving uncoated polymer, and remained unchanged in the dogs receiving the enteric coated polymer. Thus, uncoated polymer interfered with the normal absorption of zinc, ampicillin, and phenobarbital; whereas the enterically coated polymer did not interfere with absorption.

Example 4

Six male, 250 g, Sprague Dawley rats were placed on ad lib regular rat chow and ad lib 10% aqueous ethanol solution. Each rat was gavaged with a daily dose of 6.3 mg of cobalt(II) as an aqueous solution of the acetate. All rats developed severe congestive heart failure. All of the rats were given furosemide as a once per day gavaged dose of 4 mg. All of the rats became resistant to the diuretic effects of furosemide. After five days on furosemide, three of the rats were additionally placed on polymer prepared as in Example 2. The three control rats continued to retain fluid at a rate of 1.5 g per day while the rats on the enterically coated polymer increased the water excreted in their feces and had a net fluid loss of 4.7 g per day.

Example 5

Nine male, 600 g, Sprague Dawley rats underwent bilateral total nephrectomy. During the same surgery, gastric feeding tubes were placed in all of the rats and three rats also had tubes placed into the proximal to mid jejunum. All rats were then given normal daily caloric intakes using a liquid rat diet gavaged through the gastric feeding tubes. All rats had free access to water but refused it. Three rats were followed as a control group receiving only the liquid diet. Three rats were given the liquid diet and also received 0.11 g of a polymer prepared by the aqueous reaction of acrylic acid, sodium hydroxide, sodium persulfate, and trimethylolpropane triacrylate similar to that described in Buchholz, F. L. and Graham, A. T. "Modern Superabsorbent Polymer Technology," John Wiley & Sons (1998). The polymer was suspended in soy oil and gavaged into the stomach through the gastric feeding tube. The three rats with the jejunal tubes received the same polymer ("CLP") gavaged into the jejunum while their liquid diet was gavaged through the gastric feeding tube. All rats were followed with periodic sampling of blood for determination of chemistries. The mean rate of rise of the blood urea nitrogen (BUN) and serum creatinine were calculated for each group:

|  | BUN (mg/dL/hr) | Creatinine (mg/dL/hr) |
| --- | --- | --- |
| Control rats | 7.83 | 0.33 |
| Gastric CLP rats | 6.83 | 0.35 |
| Jejunal CLP rats | 4.50 | 0.19 |

Thus, the rate of increase of BUN after total nephrectomy is 81% of control rates for rats receiving CLP intragastrically and 57% of control rates for rats receiving CLP into the jejunum without exposure to the stomach. Similarly, the rate of rise of serum creatinine is 104% of control values for rats receiving CLP via the stomach and 58% of control values for rats receiving CLP directly into the jejunum.

Example 6

Three samples of a bead form polyacrylate polymer prepared according to Example 1 were sealed into filter-paper bags and immersed into a sodium phosphate/sodium chloride solution with pH 6.8 and weighed every thirty minutes to determine the extent of fluid absorption. Three samples of an irregularly shaped polyacrylate polymer prepared as described in Buchholz, F. L. and Graham, A. T. "Modern Superabsorbent Polymer Technology," John Wiley & Sons (1998) were sealed into filter-paper bags and immersed into a sodium phosphate/sodium chloride solution with pH 6.8. Weights were recorded to determine the extent of fluid absorption. The irregularly shaped polymer reached its maximum fluid absorption after two hours. The bead form of polymer reached its maximum fluid absorption after 10 hours.

Examples 7-10

A polymer was prepared as described in Example 1. The polymer was administered to a dog, together or without administration of amlodipine, an anti-hypertensive, and blood pressure was measured as indicated in Table A below.

TABLE A

| Example | CLP dose (g/kg/day) | amlodipine dose (mg/kg/day) | systolic pressure (mm Hg) | diastolic pressure (mmHg) |
|---|---|---|---|---|
| 7 | 0 | 40 | 155 | 105 |
| 8 | 1.0 | 42 | 165 | 110 |
| 9 | 1.5 | 5 | 155 | 100 |
| 10 | 2.0 | 0 | 145 | 90 |

Example 11

A polymer prepared according to Example 1 was administered to a patient, and the effects on hypertension were monitored. Before starting the polymer, the patient was found to have average systolic blood pressure of 169 mm Hg and average diastolic blood pressure of 92.5 mm Hg. While ingesting 10 g of the polymer daily, the patient's systolic blood pressure decreased to 141.5 mm Hg and the diastolic blood pressure decreased to 80 mm Hg. All medications other than the polymer were kept constant, including the patient's antihypertensive medications.

What is claimed is:

1. A method for treating a fluid overload state in a patient in need thereof, the method comprising directly delivering to the intestinal tract of the host an effective amount of a water-absorbent polymer, wherein the water-absorbent polymer is capable of absorbing at least 10 times its weight in physiological saline, wherein the water-absorbent polymer is not directly exposed to the stomach prior to delivery to the intestinal tract and wherein the fluid overload stat is congestive heart failure, cirrhosis of the liver, nephrosis, ascites, renal disease, edema associated with chemotherapy, pre-menstrual fluid overload, or preeclampsia.

2. The method of claim 1, wherein the polymer is enterically coated and the method of delivery is oral administration.

3. The method of claim 1, wherein the polymer is capable of absorbing at least 20 times its weight in physiological saline.

4. The method of claim 1, wherein the polymer is capable of absorbing at least 30 times its weight in physiological saline.

5. The method of claim 1, wherein the polymer is capable of absorbing at least 40 times its weight in physiological saline.

6. The method of claim 1, wherein the polymer is formed by polymerizing acrylate containing monomers.

7. The method of claim 1, wherein the polymer is formed by polymerizing a monomer comprising acrylic acid or salts thereof.

8. The method of claim 1, wherein the polymer is a polysaccharide.

9. The method of claim 1, wherein the polymer is enterically coated and the enteric coating is selected from at least one of hydroxypropylmethylcellulose, hydroxypropylmethylcellulose phthalate, methacrylic acid polymers, or polymers of derivatives of methacrylic acid.

10. The method of claim 1, wherein the polymer is placed within an enterically coated capsule.

11. The method of claim 1, wherein the polymer is placed within an enterically coated capsule and the enteric coating is selected from at least one of: hydroxypropylmethylcellulose, hydroxypropylmethylcellulose phthalate, methacrylic acid polymers, or polymers of derivatives of methacrylic acid.

12. The method according to claim 1, wherein the fluid overload state is renal disease.

13. The method of claim 1, wherein the fluid overload state is congestive heart failure.

* * * * *